United States Patent
Wang et al.

(10) Patent No.: US 8,426,136 B2
(45) Date of Patent: Apr. 23, 2013

(54) EPIGENETIC MODIFICATIONS AT TNFα AS BIOMARKERS FOR SENSITIVITY TO SMAC MIMETIC-INDUCED APOPTOSIS

(75) Inventors: Lai Wang, Dallas, TX (US); Brandon L. Probst, Wylie, TX (US)

(73) Assignee: Joyant Pharmaceuticals, Inc., Dallas, TX (US)

( * ) Notice: Subject to any disclaimer, the term of this patent is extended or adjusted under 35 U.S.C. 154(b) by 472 days.

(21) Appl. No.: 12/751,976

(22) Filed: Mar. 31, 2010

(65) Prior Publication Data
US 2010/0279948 A1    Nov. 4, 2010

Related U.S. Application Data

(60) Provisional application No. 61/168,191, filed on Apr. 9, 2009.

(51) Int. Cl.
*C12Q 1/68* (2006.01)

(52) U.S. Cl.
USPC .............................. 435/6.13; 435/377; 514/2.3

(58) Field of Classification Search ........................ None
See application file for complete search history.

(56) References Cited

PUBLICATIONS

Li, et al., Science vol. 305, pp. 1471-1474 (2004).*

* cited by examiner

*Primary Examiner* — Jim Ketter
(74) *Attorney, Agent, or Firm* — Richard Aron Osman

(57) ABSTRACT

The invention provides a method for determining sensitivity of a cell population to apoptosis induced by Smac mimetics as a single agent or in combination with other chemodrugs, which method comprises assaying for an epigenetic modification at the TNFα locus in the cell population as compared to the TNFα locus in a cell population not sensitive to apoptosis induced by Smac mimetics as a single agent or in combination with other chemodrugs, wherein the presence of the epigenetic modification indicates that the cell population is sensitive to apoptosis induced by Smac mimetics as a single agent or in combination with other chemodrugs.

20 Claims, 7 Drawing Sheets

EPIGENETIC MODIFICATIONS AT TNFα AS BIOMARKERS FOR SENSITIVITY TO SMAC MIMETIC-INDUCED APOPTOSIS

CROSS-REFERENCE TO RELATED APPLICATIONS

This application is a non-provisional of U.S. Application Ser. No. 61/168,191 filed on Apr. 9, 2009. The contents of the application listed in this paragraph are fully incorporated by reference herein.

TECHNICAL FIELD

The field of the invention is biomarkers for sensitivity to Smac mimetic-induced apoptosis. The biomarkers of the invention include epigenetic modifications at the TNFα locus. These biomarkers are useful for predicting the sensitivity of the cell population to apoptosis induced by Smac mimetics (as a single agent or in combination with other chemodrugs).

BACKGROUND ART

Apoptosis plays a central role in the development and homeostasis of all multi-cellular organisms. Abnormal inhibition of apoptosis is a hallmark of cancer and autoimmune diseases, whereas excessive activation of cell death is implicated in neuro-degenerative disorders such as Alzheimer's disease. Pro-apoptotic chemotherapeutic drugs provide a recent approach to overcoming the clinical problem of drug resistance. See, e.g., Makin, et al., *Cell Tissue Res.* 301:143-52 (2000).

The mechanism of apoptosis is conserved across species and executed with a cascade of sequential activation of proteases called caspases. Once activated, these caspases are responsible for proteolytic cleavage of a broad spectrum of cellular targets that ultimately lead to cell death. IAPs (inhibitor-of-apoptosis proteins) regulate apoptosis by inhibiting caspases; and a protein called Smac ("Smac" stands for second mitochondria-derived activator of caspases, and is a mitochondrial protein) binds to and inhibits IAPs, and thereby promotes caspase activation.

Defective apoptosis regulation can confer resistance to many current treatment protocols, leading to tumor growth. This may occur as a result of overexpression of IAPs, which inhibit the caspases that would otherwise initiate apoptosis. Alternatively, deregulation can occur as a result of underproduction of the Smac peptides that act to inhibit IAP activity. Deficiency of Smac can thus allow IAP to prevent apoptosis from occurring when it should, and a Smac mimetic like the present compounds can replace the activity of Smac and thus promote desired apoptosis.

Debatin, et al., WO 03/086470, describes Smac-peptides as therapeutic agents useful against cancer and autoimmune diseases; they are reported to act by sensitizing the cells toward TRAIL-induced or anticancer drug-induced apoptosis. (TRAIL stands for TNFα related apoptosis-inducing ligand). See also Li, et al., *Science* 305:1471-1474 (2004). Debatin provides in vivo evidence that Smac induces the eradication of certain tumors such as glioblastoma tumor models in animals when administered in combination with TRAIL. According to Debatin, aggressive cancer phenotypes, which result from deregulation of signaling pathways, commonly fail to undergo apoptosis when they otherwise would, allowing rapid and abnormal tissue growth. Bockbrader, et al., disclose efficacy of Smac mimic compounds on breast cancer cell lines when used in conjunction with TRAIL or etoposide, or when used in cells that express TRAIL at relatively high levels. *Oncogene* 24:7381-7388 (2005).

Similarly, according to Debatin, defects in apoptosis regulation play a key role in the pathogenesis of autoimmune disorders, including lupus erythematodes disseminatus and rheumatoid arthritis. Accordingly, compounds that mimic the activity of Smac can treat some of the effects of such conditions.

The protein Smac has been shown to inhibit a wide variety of IAPs, and is believed to be a key regulator of apoptosis in mammals. See Du, et al., *Cell* 102:33-43 (2000); Verhagen et al., *Cell* 102:43-53 (2000); and Vucic et al., *Biochem. J.* 385(1):11-20 (2005). N-terminal Smac-derived peptides and mimetics have been shown to similarly inhibit IAPs, and promote caspase-8 activation. See Petersen, et al., *Cancer Cell* 12:445-456 (2007); Varfolomeev, et al., *Cell* 131:669-681 (2007); and Vince, et al., *Cell* 131:682-693 (2007).

These studies further showed that TNFα, a death receptor ligand, is the major actor in cancer cell apoptosis induced by Smac mimetics. IAPs are components of TNFR (tumor necrosis factor receptor), so IAP inhibitors can divert TNFR signaling from an NF-κB-mediated pro-inflammatory signal, to an anti-inflammatory apoptotic signal. Acute reduction in these IAPs activates the NF-κB pathways and causes autocrine TNFα production, which in turn leads to TNFR occupancy, caspase-8 activation, and cell death.

Eukaryotic DNA is packaged into chromatin which appears as a series of "beads on a string," with the beads being the individual nucleosomes. Kornberg & Lorch, *Cell* 98:285-294 (1999). Each nucleosome consists of eight core histone proteins (two each of H3, H4, H2A and H2B), which are wrapped by 147 base pairs of DNA in a left-handed superhelix, forming the intact nucleosome. Luger, et al., *Nature* 389:251-260 (1997).

Several factors, including DNA methylation, histone modifications, and small nuclear RNAs, have been implicated in the regulation of transcription from chromatin, and are referred to as "epigenetic regulations." Epigenetic mechanisms are essential for development, cell differentiation, and protection against viral genomes, and seem to be critical for the integration of endogenous and environmental signals during the life of a cell or an organism. By analogy, deregulation of epigenetic mechanisms has been associated with a variety of human diseases, most notably cancer.

Different types of epigenetic modifications are closely linked and often act in self-reinforcing manner in the regulation of different cellular processes. DNA methylation and histone acetylation are major epigenetic modifications that are dynamically linked in the epigenetic control of gene expression and their deregulation plays an important role in tumorigenesis. See Feinberg, et al., *Nat. Rev. Genet.* 7:21-33 (2006); Jones & Baylin, *Nat. Rev. Genet.* 3:415-428 (2002). Recent studies suggested that an intimate communication and mutual dependence exists between histone acetylation and DNA methylation in the process of gene silencing. Communication between histone acetylation and cytosine methylation may proceed in both directions. In one scenario, DNA methylation may be the primary mark for gene silencing that triggers events leading to non-permissive chromatin state. In another scenario, the loss of histone acetylation may serve as the initial event of gene silencing, which is followed by DNA methylase targeting and induction of local DNA hypermethylation. See Vaissiere, et al., *Mut. Res.* 659:40-48 (2008).

DISCLOSURE OF THE INVENTION

Provided herein are methods useful for determining the sensitivity of a cell population to apoptosis induced by Smac mimetics (as a single agent or in combination with other chemodrugs) by analyzing the epigenetic status of the TNFα promoter. Both DNA-methylation and histone modifications may play important roles in the epigenetic regulation of TNFα expression and may correlate with sensitivity of a cell population to apoptosis induced by Smac mimetics (as a single agent or in combination with other chemodrugs). Thus, these epigenetic events at the TNFα promoter could serve as biomarkers for sensitivity of tumor cells to chemotherapeutic treatments such as Smac mimetics, as a single agent or in combination with other chemodrugs, as described hereafter.

Thus, in one aspect, provided herein is a method for determining the sensitivity of a cell population to apoptosis induced by Smac mimetics (as a single agent or in combination with other chemodrugs), which method comprises assaying for an epigenetic alteration at the TNFα locus in the cell population, wherein the presence/absence of the epigenetic modification indicates that the cell population is sensitive to apoptosis induced by Smac mimetics (as a single agent or in combination with other chemodrugs). Without being bound by theory, the present method is believed to base on the finding that such epigenetic modification leads to TNFα expression induced by a Smac mimetic, thus making the cell population sensitive to apoptosis induced by Smac mimetics (as a single agent or in combination with other chemodrugs).

Also provided herein is a method for sensitizing a cell population to apoptosis induced by Smac mimetics (as a single agent or in combination with other chemodrugs), which method comprises treating the cell population with an agent which alters an epigenetic modification at the TNFα locus.

Further provided herein is a method of inducing apoptosis in a cell population, which method comprises: a) determining the sensitivity to apoptosis induced by Smac mimetics (as a single agent or in combination with other chemodrugs) of the cell population by assaying for an epigenetic alteration at the TNFα locus in the cell population; and b) treating the cell population with an apoptosis-inducing agent comprising a Smac mimetic if the cell population is sensitive to Smac mimetic-induced apoptosis.

Still further provided herein is a method of inducing apoptosis in a cell population, which method comprises treating the cell population with an apoptosis-inducing agent comprising a Smac mimetic and an agent that changes an epigenetic modification at the TNFα locus.

DETAILED DESCRIPTION OF THE INVENTION

Figure 1:
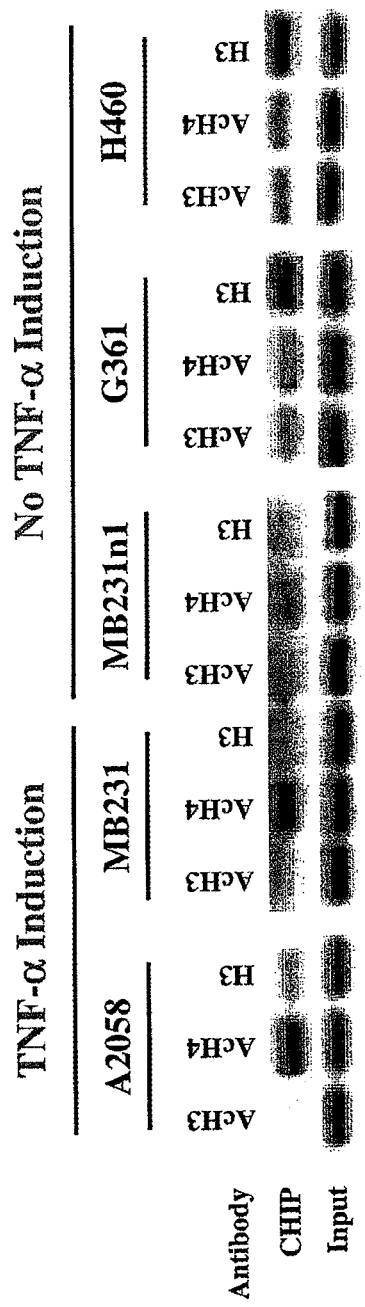
FIG. 1. Acetyl-H4 levels at the TNFα locus correlate with Smac mimetic-induced TNFα expression.

Smac mimetics have been used as a new generation of apoptosis-inducing agents in killing cancer cells by antagonizing the activity of IAPs such as XIAP, cIAP1, and cIAP2. However, there remains a need for a treatment of cells that are resistant to apoptosis induced by Smac mimetics, as a single agent or in combination with other chemodrugs. The resistance phenotype may be related to the lack of TNFα expression in response to Smac mimetic treatment in these cell populations. Activation of the NF-κB signaling pathway leads to the induction of many genes. Sensitive cell lines already secrete TNFα before any treatment (Petersen, et al., *Cancer Cell* 12:445-456 (2007)), although in most cases TNFα secretion is further increased in these same cell lines upon treatment with Smac mimetics.

Thus, cancer cells can generally be defined by their resistance or sensitivity to Smac mimetic-induced apoptosis. One type of cancer cells is sensitive to Smac mimetic-induced apoptosis. In this type of cells, Smac mimetics induce or enhance TNFα synthesis and secretion and render the cells sensitive to TNFα-induced apoptosis by forming a death domain kinase RIP1-dependent caspase-8-activating complex. Another type of cancer cells does not respond to Smac mimetic treatment. In these cells, treatment with a Smac mimetic fails to induce TNFα secretion. See Wu, et al., *Cell* 131:655-658 (2007).

The methods provided herein are useful for distinguishing these two types of cancer cells by analyzing the epigenetic alterations at the TNFα locus in such cells. Certain epigenetic alterations, such as acetylation of histone H4, were found to correlate with sensitivity of such cell population to Smac mimetic-induced apoptosis.

The present invention may be understood more readily by reference to the following detailed description of the preferred embodiments of the invention and the Examples included herein. It is to be understood that the terminology used herein is for the purpose of describing specific embodiments only and is not intended to be limiting.

DEFINITIONS

Unless defined otherwise, all technical and scientific terms used herein have the same meaning as is commonly understood by one of ordinary skill in the art to which this invention belongs. All patents, patent applications (published or unpublished), and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular form "a", "an", and "the" include plural references unless indicated otherwise. For example, "a" dimer includes one of more dimers.

A "Smac mimetic" is a molecule that has the function of inhibiting the activity of IAP proteins by mimicking the activity of the Smac N-terminal AVPI peptide. Smac mimetics have been described; see Fesik, et al., WO 2002030959; McLendon, et al., WO 2002096930; Shi, WO 2002026775; Debatin, et al., WO 2003086470; Alnemri, WO 2003010184; U.S. Pat. Publ. No. 20020132786; U.S. Pat. Publ. No. 20020160975; U.S. Pat. Publ. No. 20020177557; U.S. Pat. No. 6,608,026; WO 2006091972; WO 2005084317; Harran, et al., U.S. Pat. No. 7,309,792; WO 2008014263; WO 2008014252 The monovalent smac mimetics are designed to mimic the binding of a single AVPI binding motif to IAP proteins, whereas the bivalent compounds contain two AVPI binding motif mimetics tethered together through a linker.

Studies from several groups have clearly demonstrated that both monovalent and bivalent Smac mimetics not only enhance the antitumor activity of other anticancer agents but also can induce apoptosis as single agents in a subset of human cancer cell lines in vitro and are capable of achieving tumor regression in animal models of human cancer. In general, bivalent Smac mimetics are 100-1000 times more potent than their corresponding monovalent Smac mimetics in induction of apoptosis in tumor cells.

As used herein, an "epigenetic modification" is an inheritable change in gene function that occurs without a change in the DNA sequence. Epigenetic modifications include DNA methylation, histone modification (e.g., acetylation), and RNA interference, etc. In addition, "epigenetic modifications" as used herein may also include chromosomal binding of proteins that are responsible for DNA methylation, histone modification (e.g., acetylation), and RNA interference, etc., as well as proteins that binds to modified histones or methylated DNA.

As used herein, the "TNFα locus" refers to the genomic sequence which includes the promoter, the exons, the introns, and the intergenic regions both upstream and downstream of the TNFα gene.

The terms "sensitize" and "sensitizing," as used herein, refer to making, through the administration of a first agent (e.g., a histone deacetylase (HDAC) inhibitor), a cell population more susceptible, or more responsive, to the biological effects (e.g., promotion or retardation of an aspect of cellular function including, but not limited to, cell division, cell growth, proliferation, invasion, angiogenesis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least 10%, at least 20%, at least 30%, at least 40%, at least 50%, at least 60%, at least 70%, at least 80%, at least 90%, at least 100%, at least 150%, at least 200%, at least 350%, at least 300%, at least 350%, at least 400%, at least 450%, or at least 500% over the response in the absence of the first agent.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

MODES OF CARRYING OUT THE INVENTION

One aspect of the invention is a method for determining sensitivity of a cell population to Smac mimetic-induced apoptosis as a single agent or in combination with other chemodrugs, which method comprises assaying for an epigenetic modification at the TNFα locus in the cell population, wherein the presence/absence of the epigenetic modification indicates that the cell population is sensitive to apoptosis induced by Smac mimetics as a single agent or in combination with other chemodrugs.

The presence/absence of certain epigenetic modifications is determined in relation to a background cell population. For example, a cell population that is known to be sensitive to apoptosis induced by Smac mimetics (as a single agent or in combination with other chemodrugs) may be used as a positive control while a cell population that is known to be resistant may be used as a negative control. Alternatively, a panel of both sensitive and resistant cell populations can be analyzed for such epigenetic modification and a standard curve may be constructed from such survey, and analysis result from a cell population may be compared to such standard curve in order to determine the level of epigenetic modification and sensitivity of such cell population. In the case where a tumor sample from a patient is analyzed, similar tumor samples from other patients that have been shown to be sensitive/resistant to apoptosis induced by Smac mimetics (as a single agent or in combination with other chemodrugs) may be used as positive/negative controls.

Epigenetic Modifications at the TNFα Locus

A major type of epigenetic modification is the post-translational modification of histone proteins. The N-terminal domains of histone proteins H3 and H4 are subject to a variety of modifications, including methylation, acetylation, phosphorylation, ubiquitination, and ADP-ribosylation. Zhang & Reinberg, *Genes Dev.* 15:2343-2360 (2001); Sims, et al., *Trends Genet.* 19:629-639 (2003). These modifications occur especially at lysine, serine, and arginine residues. Research into these modifications has led to the realization that chromatin is not merely a scaffolding structure, but also a dynamic entity capable of regulating gene expression and cellular functions. This has led to the notion of the "histone code," which postulates that the type and number of histone N-terminal tail modifications serve as an epigenetic regulatory mechanism governing specific transcriptional states and biological outcomes Strahl & Allis, *Nature* 403:4145 (2000); Turner, *Cell* 111:285-291 (2002); Jenuwein & Allis, *Science* 293:1074-1079 (2001); Iizuka & Smith, *Curr. Opin. Genet. Dev.* 13:154-160 (2003). Studies supporting the notion of a "histone code" have demonstrated that histone modifications participate in a variety of essential biological processes, including gene activation, gene silencing, gene repression, and X chromosome inactivation. Lachner & Jenuwein, *Curr. Opin. Cell Biol.* 14:286-298 (2002); Lachner, et al., *J. Cell Sci.* 116:2117-2124 (2003). The histone code may be characterized by single histone modifications or by patterns of histone modifications. Berger, *Curr. Opin. Genet. Dev.* 12:142148 (2002).

A list of currently known histone modifications, their proposed functions and responsible enzymes is provided in Table 1:

TABLE 1

Types of Histone Modifications, Sites of Modification, Proposed Functions and Enzymes Involved

| Histone | Site | Histone-modifying Enzymes | Proposed Function |
|---|---|---|---|
| Acetylation | | | |
| H2A | Lys4 (*S. cerevisiae*) | Esa1 | transcriptional activation |
|  | Lys5 (mammals) | Tip60, p300/CBP | transcriptional activation |
|  | Lys7 (*S. cerevisiae*) | Hat1 | unknown |
|  |  | Esa1 | transcriptional activation |

TABLE 1-continued

Types of Histone Modifications, Sites of Modification, Proposed Functions and Enzymes Involved

| Histone | Site | Histone-modifying Enzymes | Proposed Function |
|---|---|---|---|
| H2B | Lys5 | p300, ATF2 | transcriptional activation |
| | Lys11 (*S. cerevisiae*) | Gcn5 | transcriptional activation |
| | Lys12 (mammals) | p300/CBP, ATF2 | transcriptional activation |
| | Lys15 (mammals) | p300/CBP, ATF2 | transcriptional activation |
| | Lys16 (*S. cerevisiae*) | Gcn5, Esa1 | transcriptional activation |
| | Lys20 | p300 | transcriptional activation |
| H3 | Lys4 (*S. cerevisiae*) | Esa1 | transcriptional activation |
| | | Hpa2 | unknown |
| | Lys9 | unknown | histone deposition |
| | | Gcn5, SRC-1 | transcriptional activation |
| | Lys14 | unknown | histone deposition |
| | | Gcn5, PCAF | transcriptional activation |
| | | Esa1, Tip60 | transcriptional activation DNA repair |
| | | SRC-1 | transcriptional activation |
| | | Elp3 | transcriptional activation (elongation) |
| | | Hpa2 | unknown |
| | | hTFIIIC90 | RNA polymerase III transcription |
| | | TAF1 | RNA polymerase II transcription |
| | | Sas2 | euchromatin |
| | | Sas3 | transcriptional activation (elongation) |
| | | p300 | transcriptional activation |
| | Lys18 | Gcn5 | transcriptional activation, DNA repair |
| | | p300/CBP | DNA replication, transcriptional activation |
| | Lys23 | unknown | histone deposition |
| | | Gcn5 | transcriptional activation, DNA repair |
| | | Sas3 | transcriptional activation (elongation) |
| | | p300/CBP | transcriptional activation |
| | Lys27 | Gcn5 | transcriptional activation |
| | Lys56 (*S. cerevisiae*) | Spt10 | transcriptional activation DNA repair |
| H4 | Lys5 | Hat1 | histone deposition |
| | | Esa1, Tip60 | transcriptional activation DNA repair |
| | | ATF2 | transcriptional activation |
| | | Hpa2 | unknown |
| | | p300 | transcriptional activation |
| | Lys8 | Gcn5, PCAF | transcriptional activation |
| | | Esa1, Tip60 | transcriptional activation DNA repair |
| | | ATF2 | transcriptional activation |
| | | Elp3 | transcriptional activation (elongation) |
| | | p300 | transcriptional activation |
| | Lys12 | Hat1 | histone deposition telomeric silencing |
| | | Esa1, Tip60 | transcriptional activation DNA repair |
| | | Hpa2 | unknown |
| | | p300 | transcriptional activation |
| | Lys16 | Gcn5 | transcriptional activation |
| | | MOF (*D. melanogaster*) | transcriptional activation |
| | | Esa1, Tip60 | transcriptional activation DNA repair |
| | | ATF2 | transcriptional activation |
| | | Sas2 | euchromatin |
| | Lys91 (*S. cerevisiae*) | Hat1/Hat2 | chromatin assembly |
| Methylation | | | |
| H1 | Lys26 | Ezh2 | transcriptional silencing |
| H3 | Lys4 | Set1 (*S. cerevisiae*) | permissive euchromatin (di-Me) |
| | | Set7/9 (vertebrates) | transcriptional activation (tri-Me) |
| | | MLL, ALL-1 | transcriptional activation |
| | | Ash1 (*D. melanogaster*) | transcriptional activation |

TABLE 1-continued

Types of Histone Modifications, Sites of Modification, Proposed Functions and Enzymes Involved

| Histone | Site | Histone-modifying Enzymes | Proposed Function |
|---|---|---|---|
| | Arg8 | PRMT5 | transcriptional repression |
| | Lys9 | Suv39h, Clr4 | transcriptional silencing (tri-Me) |
| | | G9a | transcriptional repression genomic imprinting |
| | | SETDB1 | transcriptional repression (tri-Me) |
| | | Dim-5 (*N. crassa*), Kryptonite (*A. thaliana*) | DNA methylation (tri-Me) |
| | | Ash1 (*D. melanogaster*) | transcriptional activation |
| | Arg17 | CARM1 | transcriptional activation |
| | Lys27 | Ezh2 | transcriptional silencing X inactivation (tri-Me) |
| | | G9a | transcriptional silencing |
| | Lys36 | Set2 | transcriptional activation (elongation) |
| | Lys79 | Dot1 | euchromatin transcriptional activation (elongation) checkpoint response |
| H4 | Arg3 | PRMT1 | transcriptional activation |
| | | PRMT5 | transcriptional repression |
| | Lys20 | PR-Set7 | transcriptional silencing (mono-Me) |
| | | Suv4-20h | heterochromatin (tri-Me) |
| | | Ash1 (*D. melanogaster*) | transcriptional activation |
| | | Set9 (*S. pombe*) | checkpoint response |
| | Lys59 | unknown | transcriptional silencing |

Phosphorylation

| Histone | Site | Histone-modifying Enzymes | Proposed Function |
|---|---|---|---|
| H1 | Ser27 | unknown | transcriptional activation, chromatin decondensation |
| H2A | Ser1 | unknown | mitosis, chromatin assembly |
| | | MSK1 | transcriptional repression |
| | Thr119 (*D. melanogaster*) | NHK1 | mitosis |
| | Ser122 (*S. cerevisiae*) | unknown | DNA repair |
| | Ser129 (*S. cerevisiae*) | Mec1, Tel1 | DNA repair |
| | Ser139 (mammalian H2AX) | ATR, ATM, DNA-PK | DNA repair |
| H2B | Ser10 (*S. cerevisiae*) | Ste20 | apoptosis |
| | Ser14 (vertebrates) | Mst1 | apoptosis |
| | | unknown | DNA repair |
| | Ser33 (*D. melanogaster*) | TAF1 | transcriptional activation |
| H3 | Thr3 | Haspin/Gsg2 | mitosis |
| | Ser10 | Aurora-B kinase | mitosis, meiosis |
| | | MSK1, MSK2 | immediate-early gene activation |
| | | IKK-α | transcriptional activation |
| | | Snf1 | transcriptional activation |
| | Thr11 (mammals) | Dlk/Zip | mitosis |
| | Ser28 (mammals) | Aurora-B kinase | mitosis |
| | | MSK1, MSK2 | immediate-early activation |
| H4 | Ser1 | unknown | mitosis, chromatin assembly |
| | | CK2 | DNA repair |

Ubiquitylation

| Histone | Site | Histone-modifying Enzymes | Proposed Function |
|---|---|---|---|
| H2A | Lys119 (mammals) | Ring2 | spermatogenesis |
| H2B | Lys120 (mammals) | UbcH6 | meiosis |
| | Lys123 (*S. cerevisiae*) | Rad6 | transcriptional activation euchromatin |

Sumoylation

| Histone | Site | Histone-modifying Enzymes | Proposed Function |
|---|---|---|---|
| H2A | Lys126 (*S. cerevisiae*) | Ubc9 | transcriptional repression |
| H2B | Lys6 or Lys7 (*S. cerevisiae*) | Ubc9 | transcriptional repression |
| H4 | N-terminal tail (*S. cerevisiae*) | Ubc9 | transcriptional repression |

Biotinylation

| Histone | Site | Histone-modifying Enzymes | Proposed Function |
|---|---|---|---|
| H2A | Lys9 | biotinidase | unknown |
| | Lys13 | biotinidase | unknown |
| H3 | Lys4 | biotinidase | gene expression |
| | Lys9 | biotinidase | gene expression |

TABLE 1-continued

Types of Histone Modifications, Sites of Modification, Proposed Functions and Enzymes Involved

| Histone | Site | Histone-modifying Enzymes | Proposed Function |
|---------|------|---------------------------|-------------------|
|         | Lys18 | biotinidase | gene expression |
| H4      | Lys12 | biotinidase | DNA damage response |

In a preferred embodiment, the epigenetic modification is a modification to a histone. In another preferred embodiment, the histone modification is selected from the group consisting of acetylation, methylation, phosphorylation, ubiquitination, sumoylation and biotinylation. In yet another preferred embodiment, the histone is selected from the group consisting of H1, H2A, H2B, H3 and H4.

As shown in Table 1, histone modification can lead to both transcription activation and repression. In a preferred embodiment, histone modifications that lead to activation of TNFα transcription are analyzed. In another preferred embodiment, histone modifications that lead to repression of TNFα gene expression are analyzed.

Histone acetylation is a reversible modification of specific residues in histone "tails" and is controlled by histone acetyltransferases (HATs) and HDACs that typically act as transcriptional co-activators and co-repressors, respectively. In a preferred embodiment, the histone modification is acetylation. In another preferred embodiment, acetylation of histone H4 is analyzed. In yet another preferred embodiment, the presence of a HAT is analyzed. In still another preferred embodiment, the presence of a HDAC is analyzed.

Recent findings suggest that lysine and arginine-specific methylation of histones may cooperate with other types of post-translational histone modification to regulate chromatin structure and gene transcription. Reviewed by Stallcup, Oncogene 20:3014-3020 (2001). Proteins that methylate histones on arginine residues can collaborate with other coactivators to enhance the activity of specific transcriptional activators such as nuclear receptors. Lysine methylation of histones is associated with transcriptionally active nuclei, regulates other types of histone modifications, and is necessary for proper mitotic cell divisions. The fact that some transcription factors and proteins involved in RNA processing can also be methylated suggests that protein methylation may also contribute in other ways to regulation of transcription and post-transcriptional steps in gene regulation. cDNA clones for five genetically distinct but related mammalian arginine methyltransferases have been isolated: PRMT1, PRMT2/HRMT1L1, PRMT3, CARM1, and JBP1. Lin et al., *J. Biol. Chem.* 271:15034-15044 (1996); Scott et al., *Genomics* 48:330-340 (1998); Tang et al., *J. Biol. Chem.* 273:16935-16945 (1998); Chen et al., *Science* 284:2174-2177 (1999); Pollack et al., *J. Biol. Chem.* 274:31531-31542 (1999). Lysines may accept one, two, or three methyl groups on the terminal amine group of the lysine side chain. Histone H3 lysine methyltransferase activity has been observed in several proteins containing SET domains. Rea et al., *Nature* 406:593-599 (2000); O'Carroll et al., *Mol. Cell. Biol.* 20:9423-9433 (2000). The mammalian SET domain protein SUV39H1 methylates lysine 9 of histone H3, and the SET domain was important for this activity. The ability to methylate histones was observed in some but not all SET domain proteins.

In a preferred embodiment, the histone modification is methylation. In another preferred embodiment, the presence of a arginine methyltransferase is analyzed. In yet another preferred embodiment, the presence of a lysine methyltransferase is analyzed.

Histone modifications provide the binding sites for a series of effector proteins that would affect chromatin function. Histone acetylation has been shown to facilitate the access of a number of transcription factors to the DNA. Lee, et al., *Cell* 72:73-84 (1993); Nightingale, et al., *EMBO J.* 17:2865-76 (1998); Vettese-Dadey, et al., *EMBO J.* 15:2508-18 (1996). Histone acetylation has also been shown to facilitate the passage of the RNA polymerase on chromatin. Marushige, *Proc. Natl. Acad. Sci. USA* 73:3937-41 (1976). Protein domains able to interact with chromatin and/or its modified components—like bromodomains, chromodomains or the SANT domains—can play a crucial role in the targeting process.

Histone modifications may promote transcription by providing binding sites for proteins involved in gene activation, such as those containing bromodomains. Shahbazian & Grunstein, *Annu. Rev. Biochem.* 76:75-100 (2007). The bromodomain is widely distributed among the different enzymes that acetylate, methylate or remodel chromatin. The chromatin remodeling complex SWI/SNF, which mobilizes nucleosomes and is important for transcriptional activation, appears to bind acetylated histones through a bromodomain; both the bromodomain of Snf2 and histone acetylation by SAGA or NuA4 are required for stabilization of SWI/SNF binding on nucleosome arrays. Hassan, et al. *Cell* 111:369-79 (2002). In mammalian cells, many transcription-promoting factors also contain bromodomains that bind specific acetylation sites. For example, the bromodomain in BRG1 (the catalytic subunit of SWI/SNF) has been shown to bind acetylated H4 K8, and the TBP-associated factor TAFII250 appears to bind H3 acetylated at K9 and K14. Agalioti, et al., *Cell* 111:381-92 (2002). Thus, in a preferred embodiment, the presence of a bromodomain protein is analyzed. In another preferred embodiment, the bromodomain protein is selected from the group consisting of BRM, BRG1, P300, PCAF, CBP, TAF250, GCN5, LOC330129 and MLL.

The chromodomain was first identified as a common domain between two distinct regulators of chromatin structure in Drosophila: HP1 and Polycomb. De la Cruz, et al., *BioEssays* 27:164-175 (2005). Later, chromodomains have been found in many other chromatin regulators: (i) remodeling factors involved in causing conformational changes by ATP-dependent movement of nucleosomes and (ii) histone acetyltransferases and methyltransferases. Jones, et al., *BioEssays* 22:124-137 (2000); Eissenberg, *Gene* 275:19-29 (2001). Recent work from different laboratories has shown that the HP1 chromodomain can recognize methylation of Lys 9 in histone H3, thus directing the binding of other proteins to control chromatin structure and gene expression. Apart from recognizing methyllysines, chromodomains can also serve to DNA and/or RNA recognition. The chromodomain has been found in HAT, HMT and ATP-dependent chromatinremodelling enzymes. De la Cruz, et al., *BioEssays* 27:164-175 (2005). Thus, in a preferred embodiment, the presence of a chromodomain protein is analyzed. In another preferred embodiment, the chromodomain protein is selected from the group consisting of CHD-3, CHD-4, CHD-5, CDY-1, CDY-2, TIP60, MORF4L1, SUV39H1 and SUV39H2.

The SANT domain is present in some ATP-dependent remodelling enzymes complexes: yeast Swi3p, Rsc8p, BAF155/170 and Drosophila ISWI. De la Cruz, et al., *BioEssays* 27:164-175 (2005). The general role of the SANT domain is to stabilize, through direct binding, histone N-terminal tails in a conformation favoring their binding to the modifying enzymes, and the subsequent catalytic process. It has a central role in chromatin remodelling, being the unique histone-interaction module that couples histone binding to enzyme catalysis. It is present in the two enzyme classes responsible of chromatin modifications (enzymes that catalyse the histones covalent modifications and complexes using ATP hydrolysis). The preference of the SANT domain for unmodified histone tails suggests that histone deacetylation could increase its affinity for histone tails. Interaction with unacetylated histone tails could block the binding of HATs, thus maintaining the deacetylated state. Thus, in a preferred embodiment, the presence of a SANT domain protein is analyzed. In another preferred embodiment, the SANT domain protein is selected from the group consisting of SNF2L, SNF2H, EZH1 and EZH2.

The methylation of DNA is the covalent addition of a methyl group to the five-carbon ($C^5$) position of cytosine bases in CpG dinucleotides. Methylation of cytosine is carried out by two types of DNA methyltransferases (DNMTs): de novo and maintenance methyltransferases. DNA methylation patterns are established during early development by de novo methyltransferases DNMT3A and DNMT3B. Patterns of DNA methylation are propagated with extreme fidelity by the maintenance methyltransferase DNMT1, which reproduces patterns of methylated and unmethylated CpG sites between cell generations. Thus, in a preferred embodiment, the epigenetic modification is DNA methylation.

Analyzing Epigenetic Modifications at the TNFα Locus

Histone modifications and DNA methylation at the TNFα locus may be analyzed by ChIP (chromatin immunoprecipitation) experiments. The sequence of the TNFα locus is provided as SEQ NO:1. To increase throughput, ChIP-on-chip experiments may be conducted to allow detection of histone modification or DNA methylation using microarrays or DNA chips with probes that cover the whole length of the TNFα locus or the entire promoter region.

In a preferred embodiment, the probes and primer pairs that are used for ChIP and ChIP-on-chip experiments are selected from the genomic sequences that cover the TNFα locus, including the promoter region, the exons, the introns, and the intergenic regions both upstream and downstream of the TNFα gene. DNA methylation may also be detected by bisulfite sequencing experiments or the HELP assay.

DNA methylation as well as histone acetylation and methylation have been shown to correlate with TNFα gene expression after PMA or LPS stimulation in K562 and THP-1 cells. See Sullivan, et al., *Mol. Cell. Biol.* 27:5147-5160 (2007). Alavi, et al. claims a method for determining potential TNFα expression in a cell population by determining if the TNFα promoter is methylated. WO 2008/137930. In THP-1 cells that are endotoxin-responsive, dissociation of heterochromatin-binding protein 1-alpha, demethylation of histone H3 lysine 9, increased phosphorylation of H3 serine 10, and recruitment of NF-B RelA/p65 to the TNFα promoter were shown to lead to increased TNFα mRNA. See Gazzar, et al., *J. Biol. Chem.* 282:26857-26864 (2007). Therefore, in a preferred embodiment of the invention the epigenetic modification at the TNFα locus correlates with the level of TNFα gene expression after a Smac mimetic treatment. In another preferred embodiment of the invention, the histone acetylation at the TNFα locus correlates with the level of TNFα gene expression after a Smac mimetic treatment.

Also provided herein is a method to sensitize a cell population to apoptosis induced by Smac mimetics (as a single agent or in combination with other chemodrugs) by treating the cell population with an agent that changes the epigenetic modification pattern at the TNFα locus. In a preferred embodiment, the agent is an HDAC inhibitor. In another preferred embodiment, the agent is an inhibitor of DNA methyltransferase.

A relatively wide range of structures have been identified that are able to inhibit the activity of class 1, class 2 and class 4 HDACs. See Minucci & Pelicci, *Nat. Rev. Cancer* 6:38-51 (2006). They derive from both natural sources and from synthetic routes. The first category includes molecules such as FK-228, Apicidin, Trichostatin A (TSA), and sodium butyrate. The second category includes molecules such as SAHA, AN-9 (Pivanex), CHAPs, PXD-101, Sulfonamide hydroxamic acid, MS-275, Tubacin, sodium phenyl butrate, and sodium valporate, etc. With a few exceptions, they can all be divided into chemical classes including hydroxamic acid derivatives, carboxylates, benzamides, electrophilic ketones and cyclic peptides. In a preferred embodiment, the HDAC inhibitor is selected from the group consisting of MS-275, sodium butyrate, valproic acid, Trichostatin A, and suberoylanilide hydroxamic acid.

The human genome contains four DNA methyltransferase genes, DNMT1, DNMT2, DNMT3A, and DNMT3B, that encode proteins with distinct functional specificities. Stresemann, et al., *Cancer Res.* 66:2794-2800 (2006). The most widely used DNA methyltransferase inhibitor, 5-azacytidine (5-aza-CR), is a cytidine analogue that functions as a mechanism-dependent suicide inhibitor of DNA methyltransferases. To be effective, 5-aza-CR needs to be incorporated into DNA, which requires extensive modification of the compound through metabolic pathways. DNA methyltransferases recognize 5-azacytosine as natural substrate and initiate the methylation reaction. 5-aza-CR causes substantial cytotoxicity and is not a specific inhibitor of DNA methyltransferases. Due to its ribonucleoside structure, most of the compound becomes incorporated into RNA and thereby interferes with protein translation. This problem has been addressed by the development of a deoxyribonucleoside analogue, 5-aza-2V-deoxycytidine (5-aza-CdR), which becomes more directly incorporated into DNA and causes more efficient inhibition of DNA methyltransferases. Zebularine, procaine, EGCG, and RG108 are also known as DNA methyltransferase inhibitors. In a preferred embodiment, the DNA methyltransferase inhibitor is selected from the group consisting of 5-azacytidine, zebularine, procaine, EGCG, and RG108.

A further aspect of the invention is a method to induce apoptosis in a cell population by contacting the cell population with an apoptosis-inducing agent comprising a Smac mimetic and an agent that changes the epigenetic modification pattern at the TNFα locus. In a preferred embodiment, the agent is an HDAC inhibitor. In another preferred embodiment, the agent is a DNA methyltransferase inhibitor.

In preferred embodiments, the cells are in situ in an individual diagnosed as in need of an apoptosis promoting treatment, and the contacting step is effected by administering to the individual a pharmaceutical composition including a therapeutically effective amount of the Smac mimetic, wherein the individual may be subject to concurrent or antecedent radiation or chemotherapy for treatment of a neoproliferative pathology. In particular embodiments, the pathogenic cells are of a tumor, such as glioblastoma, astrocytoma, breast cancer, prostate cancer, lung cancer, pancreatic cancer, gastric cancer, colon cancer, ovarian cancer, renal cancer, hepatoma, melanoma, lymphoma, leukemia or sarcoma.

In additional embodiments, the target cells are pro-inflammatory cells or cells of tissue subject to pathogenic inflammation and/or autoimmunity. A wide variety of diseases involve such pathogenic inflammation, including rheumatoid arthritis, diabetes, asthma, lupus, myasthenia gravis, Graves disease, inflammatory bowel disease (e.g., Crohn's disease, ulcerative colitis and related conditions), pelvic inflammatory diseases, chronic obstructive pulmonary disease (COPD), chronic bronchitis, pneumoconiosis, pulmonary emphysema, interstitial lung fibrosis, allergic rhinitis (hay fever), inflammatory cardiovascular diseases (e.g., congestive heart failure and ischemia/reperfusion injuries), atherosclerosis (including coronary artery disease), stroke, neurodegenerative diseases, such as Alzheimer's disease, multiple sclerosis and amyotrophic lateral sclerosis (ALS), neuroinflammatory diseases, organ transplant rejection, autoimmune hematological disorders, psoriasis, sclerodoma, chronic active hepatitis, primary biliary cirrhosis, glomerulonephritis, uveitis and keratoconjunctivitis.

The subject compositions encompass pharmaceutical compositions containing a therapeutically effective amount of an active, dimer-like Smac mimetic in dosage form, and a pharmaceutically acceptable excipient, such as a carrier or diluent. In some embodiments, such compositions also contain an additional therapeutic agent, such as an anti-neoproliferative chemotherapeutic agent, in addition to the Smac mimetic.

EXAMPLES

The following examples are provided to illustrate the invention and are not intended to represent or limit its scope. The Examples provide representative chemical syntheses, as well as assays for determining the bioactivity of Smac mimetics, e.g., as measured by IAP binding, procaspase-3 activation or promotion of apoptosis. These assays may also be used to screen for agents (e.g., antagonists) which potentiate such mimetic activity.

Tumor Necrosis Factorα Semiquantitative RT-PCR Protocol

This procedure describes the semi-quantitative measurement of human TNFα mRNA levels in human cell culture.

Materials:

For RNA isolation, RNAeasy miniprep kit from Qiagen or TRIzol Reagent from Invitrogen were used, along with 22-gauge needle, 1 cc syringe, and 70% EtOH.

For generation of cDNA, RNase free tubes, RNase free ddH2O, Omniscipt RT kit (Qiagen), and Oligo dT primer (IDT) were used.

For PCR Reaction, Thermocycler, Taq DNA polymerase (NEB), 10 mM dNTPS (NEB) were used.

Procedures:

Cell Treatment: cells were plated in 6 well dishes at $1.5 \times 10^5$ cells/ml in a volume of 2.5 ml, next day cells were treated −/+50 ul of 5 µM Smac Mimetic, JP1010, (final concentration: 100 nM) for 4 hr.

RNA Isolation: cells were washed 2× with 2 ml PBS followed by isolation of RNA from 6 well dishes using Qiagen RNAeasy kit or TRIzol reagent (Invitrogen) according to manufacturer's protocol. RNA isolation with TRIzol was conducted by adding 1 ml of TRIzol reagent to each well and pipetting up and down several times before transferring lysate to 1.5 ml microfuge tube. The mixture was incubated at room temperature for 5 min to allow for complete dissociation of nucleoprotein complexes followed by adding 0.2 ml of chloroform, vortexing for 15 sec and then incubating at room temperature for 2-3 min Samples were centrifuged at 12,000×g for 15 min at 4° C. and the colorless upper aqueous phase was transferred to a new microfuge tube. RNA from the solution was precipitated by the addition of 0.5 ml isopropyl alcohol and incubation at room temperature for 10 min and centrifugation at 12,000 g for 10 min at 4° C. The supernatant was removed without disturbing the RNA pellet. The pellet was washed with the addition of 0.5 ml 75% ethanol followed by centrifugation at 7,500 g for 5 min at 4° C. The ethanol was removed and RNA pellet briefly air dried and then resuspended in 30 ul RNAse free ddH20. RNA concentration was measured.

Generation of cDNA: 2 ug of total RNA was used in a 20 ul reverse transcription reaction with 2 ul 5 mM dNTPs, 2 ul 20×RT buffer, 2 ul Oligo dT primer, 1 ul diluted RNase Inhibitor (10 U/ul), 1 ul Omniscript RT, 2 ug RNA, up to 20 ul ddH2O and incubated for 1 hr. at 37° C.

Semi-quantitative RT-PCR for TNFα and Actin were performed as follows: Control semi-quantitative Actin PCR were conducted in a 25 ul reaction mixture with the following cycle condition: 94° C. 2 min, 25 cycles of 94° C. 30 s, 52° C. 30 s, 72° C. 60 s, and 72° C. 7 mM The reaction mixture contained 1 ul cDNA template, 2.5 ul 10× Thermopolymerase buffer, 0.5 ul 10 mM dNTPS, 0.25 ul 100 uM Actin Forward primer, 0.25 ul 100 uM Actin Reverse primer, 0.5 ul Taq DNA polymerase, and 20 ul ddH2O. TNFa semi quantitative PCR were conducted in a 25 ul reaction mixture with the following cycle conditions: 94° C.-2 min, 30-35 cycles (depending on cell line) of 94° C.-30 sec, 59° C.-30 sec, 72° C.-1 min, followed by 72° C. for 10 min. The reaction mixture contained 2 ul single strand cDNA template, 2.5 ul 10× Thermopolymerase buffer, 0.5 ul 10 mM dNTPs, 0.25 ul 100 uM TNFα forward primer, 0.25 ul 100 uM TNFα reverse primer, 0.5 ul Taq DNA polymerase, and 19 ul ddH2O. After PCR was completed 5 ul of 6×DNA loading dye was added to each tube and 25 ul was loaded onto 1.5% Et-Br agarose gel and run for 30 min at 150V.

Chromatin Immunoprecipitation (ChIP) Protocol

Purpose: This procedure evaluates the localization of specific proteins or their modified forms on chromatin. For our purpose to specifically evaluate the levels of modified histones and cofactors bound to the Tumor Necrosis Factor (TNFa) gene promoter.

Materials:

ChIP Lysis buffer contained 1% SDS, 10 mM EDTA, 50 mM Tris-HCl, pH8.1, 1× protease inhibitor cocktail (Roche). ChIP Dilution buffer contained 1% Triton x-100, 2 mM EDTA, 150 mM NaCl, 20 mM Tris-HCl, pH8.1, 1× protease inhibitor cocktail (Roche). Wash Buffer I contained 0.1% SDS, 1% Triton x-100, 2 mM EDTA, 150 mM NaCl, 20 mM Tris-HCl, pH8.1. Wash Buffer II contained wash buffer I with 500 mM NaCl. Wash Buffer III contained 0.25M LiCl, 1% NP-40, 1% deoxycholate, 1 mM EDTA, 10 mM Tris-HCl, pH8.1. TE buffer contained 10 mM Tris-HCl, pH 7.5, 0.1 mM EDTA. ChIP Extraction buffer contained 1% SDS, 0.1M NaHCO3. Antibodies used include anti-histone H3 (Abcam, ab1791), anti-hyperacetylated histone H4 (Millipore, 06-946), anti-dimethyl-histone H3k4 (Millipore, 07-030), anti-dimethyl histone H3K9 (Abcam, ab1220), anti-histone H4 (Millipore, 05-858), anti-acetylated H3 (Millipore, 06-599), anti-acetylated H4 (Millipore, 06-866).

Procedure:

Cells were plated on either 10 cm or 15 cm tissue culture dishes (~$1 \times 10^6$). At 80-100% confluency cells were crosslinked by the addition of 37% formaldehyde (final concentration 1%) directly to the cell medium. Medium was removed and cells washed twice with ice cold PBS. Cells were scraped into a microfuge tube and pelleted by centrifugation at 2000 rpm for 5 min at 4° C. Pellet was resuspend in 200 ul ChIP Lysis buffer per 10 cm dish or 400 ul per 15 cm dish and let sit on ice for 10 min DNA was sheared to 200-1000 bp by sonicating the lysate on ice with a Branson Model 500 Sonic Dismembranator and microtip (power output: 37%, 4×10 sec pulses with 1 min on ice between pulses). Samples were centrifuged for 10 min at 13,000 g at 4° C. and supernatant transferred to a new 1.5 ml microfuge tube. $\frac{1}{10}$ vol. of sonicated DNA was removed for INPUT and stored at −20° C. The remaining 180 ul of sonicated DNA was diluted into a total volume of 1.5 ml with ChIP Dilution Buffer. To reduce nonspecific background, diluted samples were pre-cleared with 50 ul of Salmon Sperm DNA/protein A Agarose-50% slurry (Upstate Biotechnology) for 30 min at 4° C. on Labquake tube rotator. Agarose beads were pelleted by brief centrifugation and supernatant transferred to a new microfuge tube containing the appropriate amount of immunoprecipitating antibody and incubate overnight at 4° C. with rotation. As a negative control, a no antibody or IgG immunoprecipitation was performed. 50 ul of Salmon Sperm DNA/protein A Agarose slurry was added to each tube and rotated for 1 hr at 4° C. to collect the antibody/histone complexes followed by centrifugation at 1000 rpm at 4° C. for 2 min Supernatant was aspirated off and beads were washed for 5 min on a rotating platform with 0.5 ml of each of the buffers listed in order as follows: Wash buffer I—Low Salt, one wash; Wash buffer II—High Salt, one wash; Wash buffer III—LiCl wash, one wash; TE buffer, two washes. Elute histone complex from antibody by adding 125 ul of ChIP extraction buffer and rotate at room temperature for 15 min Spin down beads and transfer supernatant to a new microfuge tube. Repeat elution step by adding 125 ul of ChIP extraction buffer and rotate 15 min. Combine the two elutions. Reverse crosslinking to isolate DNA by either of PCR purification kit or phenol/chloroform extraction. For DNA purification w/PCR kit add 5 ul RNAse A (0.5 mg/ml) and heat at 65° C. overnight. DNA isolated with Qiagen PCR purification kit according to manufacturers protocol. (note: input samples from sonication step are removed from −20° C. and treated identically). For Phenol/Chloroform purification: sample volume (including inputs) are brought to a volume of 400 ul with ChIP extraction buffer and 5 ul of proteinase K (20 mg/ml) added. Heat overnight at 65° C. to reverse crosslinking and purify used standard phenol:chloroform extraction followed by ethanol precipitation with 10 ul of 5 mg/ml glycogen. Pellets were resuspended in final volume of 50 ul. PCR was performed using 2-5 ul of sample DNA in a 25 ul rxn as follows: 2.5 ul 10× Thermopolymerase buffer, 0.5 ul 10 mM dNTPs, 0.25 ul TNFα CHIP F primer, 0.25 ul TNFα CHIP R primer, 0.5 ml Taq DNA polymerase, and Up to 25 ul with ddH2O. Thermocycler conditions: 95° C. for 2 min, followed by 34 cycles of 95° C. for 30 s, 51° C. for 30 s, 72° C. for 30 s. An additional 7 min incubation at 72° C. was performed. Gel Electrophoresis: After PCR was completed 5 ul of 6×DNA loading dye added to each tube and 25 ul was loaded onto 1.5% Et-Br agarose gel. Gel run for 30 min at 150V.

Note: the ChIP protocol was adapted from those described by Abcam, Upstate, and in *Biochem. Biophys. Res. Comm* 359:88-93 (2007).

Example 1

Acetyl-H4 Levels at the TNFα locus Correlate with Smac Mimetic Induced TNF-a Expression Acetylated H4 levels were surveyed in cell lines that are either sensitive or resistant to Smac mimetic-induced TNFα expression. In the two cell lines that are inducible, A2058 and MB231, high levels of acetylated H4 were detected (FIG. 1). On the other hand, acetylated H4 was barely detectable in three cell lines that are non-inducible, MB231n1, G361, and H460 (FIG. 1).

Example 2

Figure 2:
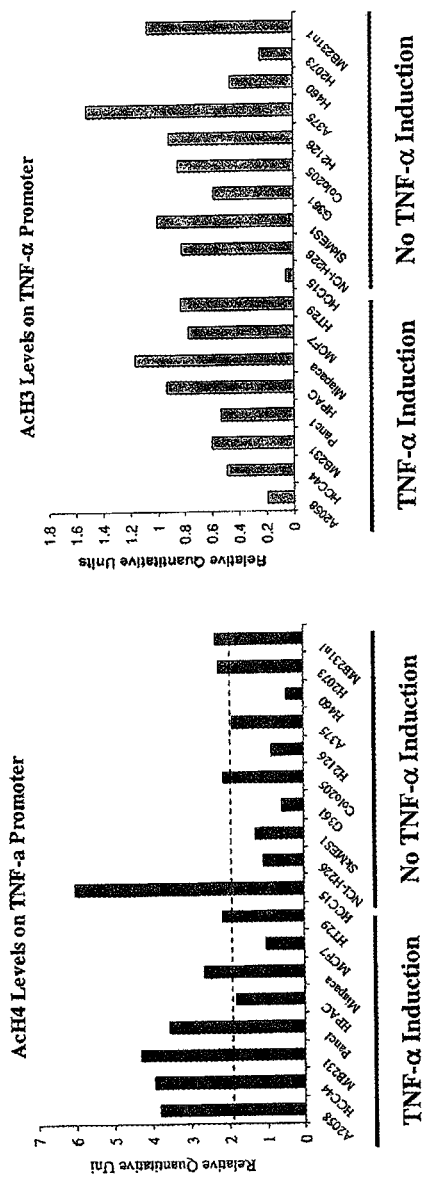
FIG. 2. Higher levels of acetylated H4 at the TNFα locus correlate with Smac mimetic-induced TNFα expression.

Higher Levels of Acetyl-H4 at the TNFα Locus Correlate with Smac Mimetic-Induced TNF-a Expression An expanded panel of cell lines that are either sensitive or resistant to Smac mimetic-induced TNFα expression was surveyed for their acetylated H4 and acetylated H3 levels. Most sensitive cell lines showed a higher level of acetylated H4 than the resistant cell lines (FIG. 2). No significant difference in acetylated H3 levels was detected between the two types of cell lines (FIG. 2). Quantified Acetyl-H3 and Acetyl-H4 levels were normalized against total H3 levels.

Example 3

Smac Mimetics do not Affect Acetylated Histone H4 Levels at the TNFα Locus

Figure 3:
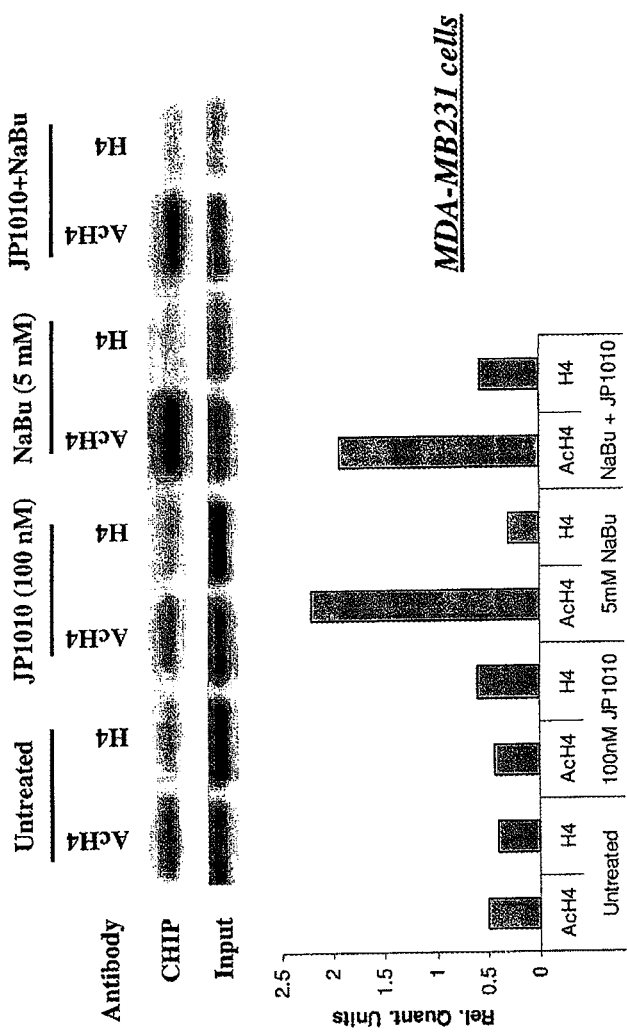
FIG. 3. Smac mimetics do not affect acetylated Histone H4 levels at the TNFα locus.

The effect of Smac mimetic JP1010 on the level of acetylated H4 was tested in MDA-MB231 cells. The addition of 100 nM of JP1010 did not change the level of acetylated H4 either alone or in combination with 5 mM NaBu (FIG. 3). However, the HDAC inhibitor NaBu increased the level of acetylated H4 for 4-5 fold (FIG. 3).

Example 4

Figure 4:
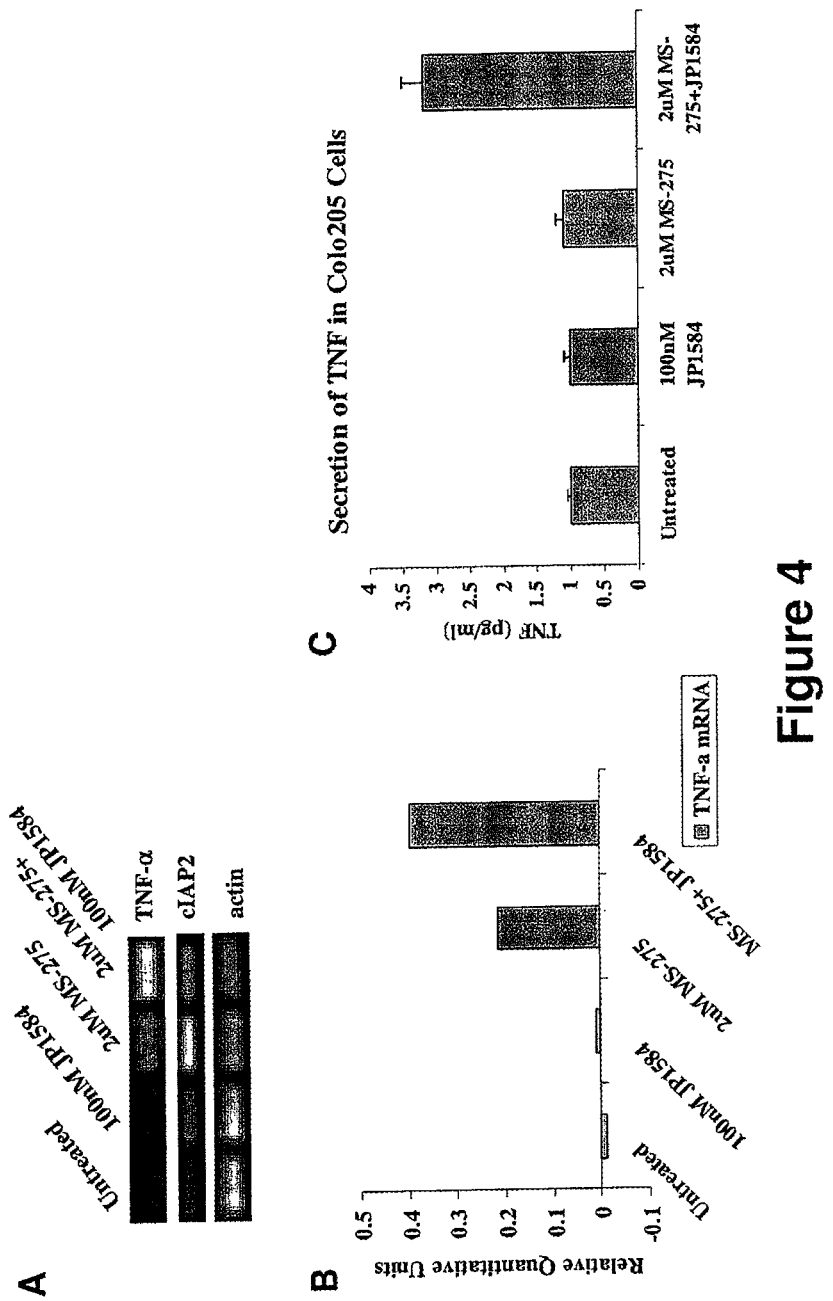
FIG. 4. HDAC inhibitor MS-275 Primes Colo205 cells for Smac mimetic-induced TNFα production.

HDAC Inhibitor MS-275 Primes Colo205 Cells for Smac Mimetic Induced TNF-a Production The effect on TNFα production by HDAC inhibitor MS-275 was examined in Colo205 cells. Both the levels of transcription, assayed by RT-PCR, and levels of protein secretion, assayed by measurement of secreted protein amount, were examined MS-275 increased production of TNFα mRNA, but not TNFα protein secretion (FIG. 4). It also increased the mRNA level of cIAP2 (FIG. 4A). When it was combined with the Smac mimetic JP1584, both the levels of TNFα transcription and protein secretion were increased (FIG. 4). However, JP 1584 alone did not increase the level of either mRNA or protein secretion of TNFα (FIG. 4).

Example 5

Figure 5:
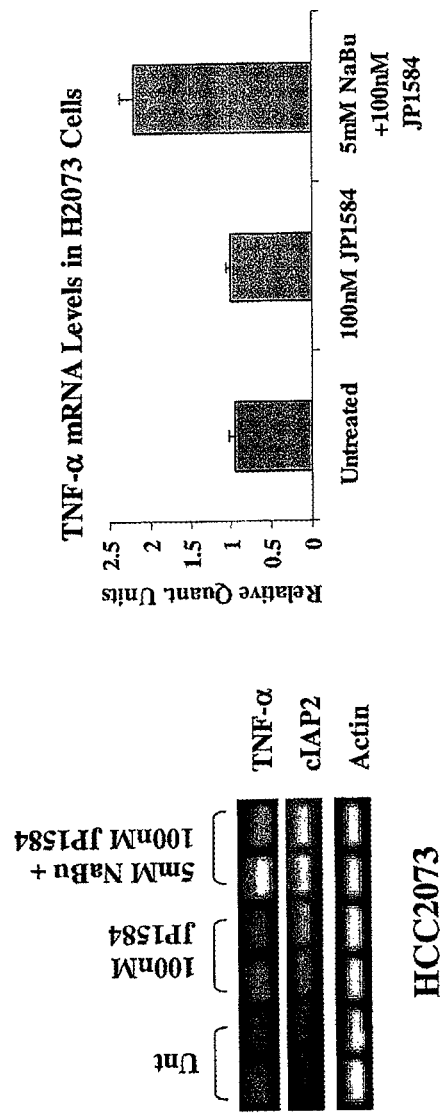
FIG. 5. Sodium butyrate (NaBu), an HDAC inhibitor, increases Smac mimetic-induced TNFα production in H2073 cells.

HDAC Inhibitor Sodium Butyrate (NaBu) Increases Smac Mimetic Induced TNF-a Production in H2073 Cells The effect on TNFα production by HDAC inhibitor NaBu was examined in H2073 cells. Both the levels of transcription, assayed by RT-PCR, and levels of protein secretion, assayed by measurement of secreted protein amount, were examined. When NaBu was combined with the Smac mimetic JP1584, both the levels of TNFα transcription and protein secretion were increased (FIG. 5). However, JP 1584 alone did not increase the level of either mRNA or protein secretion of TNFα (FIG. 5).

Example 6

Smac Mimetic does not Induce TNF-a Production in Resistant Cells

Figure 6:
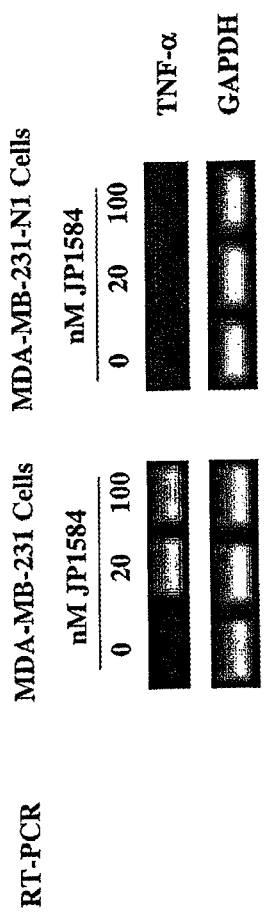
FIG. 6. Smac mimetics do not induce TNFα production in resistant cells.

TNF expression in MDA-MB-231 and MDA-MB-231-N1 cells was analyzed by RT-PCR assay after treatment with 20 nM and 100 nM of Smac mimetic, JP1584. High level TNFα expression was detected in Smac mimetic-sensitive MDA-MB-231 cells even with 20 nM of JP1584 treatment, while no TNFα expression was detectable in the resistant MDA-MB-231-N1 cells (FIG. 6).

Example 7

Figure 7:
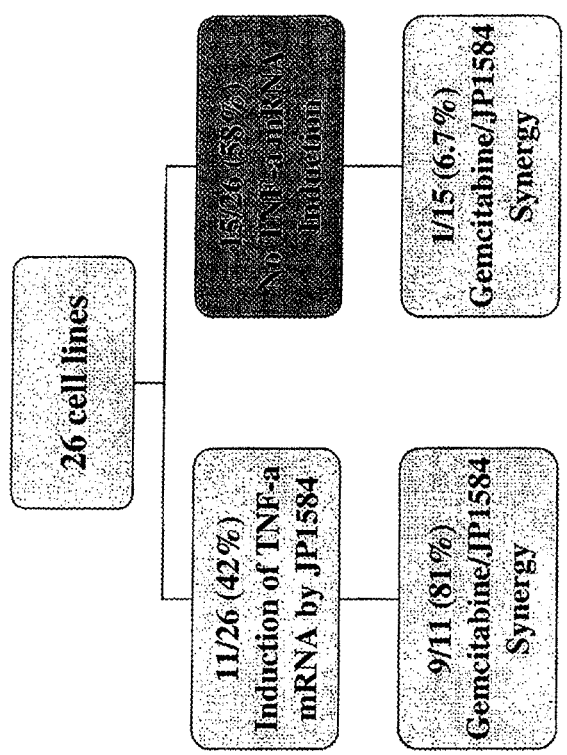
FIG. 7. Correlation between induced TNFα expression and Gemcitabine/JP1584 synergy.

Correlation between Induced TNF-a Expression and Gemcitabine/JP1584 Synergy Twenty-six cells lines were surveyed for their JP1584-induced TNFα expression and sensitivity to Gemcitabine/JP1584-induced apoptosis. Eleven out of the twenty-six cell lines (42%) had JP1584-induced TNFα expression, while 15 (58%) did not (FIG. 7). Out of the 11 cell lines that had inducible TNFα expression, 9 (81%) were also sensitive to Gemcitabine/JP1584-induced apoptosis. Out of the 15 cell lines that had no inducible TNFα expression, only one (6.7%) was also sensitive to Gemcitabine/JP1584-induced apoptosis.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

Citation of the above publications or documents is not intended as an admission that any of the foregoing is pertinent prior art, nor does it constitute any admission as to the contents or date of these publications or documents.

What is claimed is:

1. A method of inducing apoptosis in a cell population, which method comprises:
   a) determining that the cell population is sensitive to Smac mimetic-induced apoptosis by detecting an epigenetic modification at the TNFα locus in the cell population correlated with sensitivity to Smac mimetic-induced apoptosis; and
   b) contacting the cell population with a composition comprising an effective amount of a peptidyl Smac mimetic, whereby apoptosis is induced in the cell population.

2. The method according to claim 1, wherein the composition further comprises an effective amount of a chemotherapy drug.

3. The method according to claim 1, wherein the epigenetic modification is a histone modification.

4. The method according to claim 1, wherein the epigenetic modification is a histone modification that correlates with Smac-induced TNFα gene expression.

5. The method according to claim 1, wherein the epigenetic modification is a histone modification that is acetylation.

6. The method according to claim 1, wherein the epigenetic modification is a histone modification that is acetylation of H4.

7. The method according to claim 1, wherein the epigenetic modification is a histone modification that is methylation.

8. The method according to claim 1, wherein the epigenetic modification is presence of a histone acetyltransferase or a histone deacetylase.

9. The method according to claim 1, wherein the epigenetic modification is presence of an arginine methyltransferase, a lysine methyltransferase, a bromodomain protein, a chromodomain protein, or a SANT domain protein.

10. The method according to claim 1, wherein the epigenetic modification is determined by chromatin immunoprecipitation, or by ChIP-on-chip.

11. The method according to claim 1, wherein the epigenetic modification is a histone methylation determined by bisulfite sequencing or the HELP assay.

12. The method according to claim 1, wherein the epigenetic modification correlates with the level of TNFα gene expression after a Smac mimetic treatment.

13. The method according to claim 1 wherein the contacting step further comprises contacting the cell population with an agent that changes an epigenetic modification at the TNFα locus.

14. The method according to claim 1, wherein the cell population is in situ in an individual diagnosed as in need of an apoptosis promoting treatment.

15. The method according to claim 13, wherein the agent is a histone deacetylase inhibitor.

16. The method according to claim 13, wherein the agent is a histone deacetylase inhibitor selected from the group consisting of MS-275, sodium butyrate, valproic acid, Trichostatin A, and suberoylanilide hydroxamic acid.

17. The method according to claim 13, wherein the agent is a DNA methyltransferase inhibitor.

18. The method according to claim 13, wherein the cell population is in situ in an individual diagnosed as in need of an apoptosis promoting treatment, and subjecting the individual to concurrent or antecedent radiation or chemotherapy.

19. The method according to claim 6, wherein the agent is a histone deacetylase inhibitor selected from the group consisting of MS-275, sodium butyrate, valproic acid, Trichostatin A, and suberoylanilide hydroxamic acid.

20. The method of claim 19 wherein the cell population is a tumor cell population isolated from a patient.

* * * * *